US006997894B2

(12) United States Patent
Caresio

(10) Patent No.: US 6,997,894 B2
(45) Date of Patent: Feb. 14, 2006

(54) VASCULAR ACCESS CATHETER HAVING A CURVED TIP AND METHOD

(76) Inventor: Joseph F. Caresio, 1705 Golden Oak Dr., Las Vegas, NV (US) 89117

( * ) Notice: Subject to any disclaimer, the term of this patent is extended or adjusted under 35 U.S.C. 154(b) by 126 days.

(21) Appl. No.: 10/187,244

(22) Filed: Jul. 2, 2002

(65) Prior Publication Data

US 2004/0006297 A1   Jan. 8, 2004

(51) Int. Cl.
A61M 37/00 (2006.01)
A61M 3/00 (2006.01)
A61M 25/00 (2006.01)

(52) U.S. Cl. ............. 604/6.16; 604/4.01; 604/43; 604/523

(58) Field of Classification Search ........... 604/4.01, 604/5.01–5.04, 6.16, 8, 19, 27, 28, 39, 43, 604/500, 507–508, 264–266, 270–271, 523, 604/533, 534, 538, 284, 540–1, 544; 128/898; 606/108–9, 191, 194; 600/433–35
See application file for complete search history.

(56) References Cited

U.S. PATENT DOCUMENTS

| 5,037,403 A | * | 8/1991 | Garcia ..................... 604/532 |
| 5,057,073 A | * | 10/1991 | Martin ..................... 604/43 |
| 5,209,723 A | * | 5/1993 | Twardowski et al. ......... 604/43 |
| 6,042,576 A | * | 3/2000 | DeVries ..................... 604/523 |
| 6,482,169 B1 | * | 11/2002 | Kuhle ..................... 604/6.16 |
| 6,517,529 B1 | * | 2/2003 | Quinn ..................... 604/528 |
| 6,758,836 B1 | * | 7/2004 | Zawacki ..................... 604/284 |
| 2002/0188167 A1 | * | 12/2002 | Viole et al. ............. 600/16 |

* cited by examiner

*Primary Examiner*—Patricia Bianco
(74) *Attorney, Agent, or Firm*—Jeffrey Weiss; Janine Rickman Novatt; Weiss, Moy & Harris, P.C.

(57) ABSTRACT

A vascular access catheter having a curved tip. Preferably, the curved tip is formed into a substantially pig-tail shape. Where the catheter is of the double lumen variety, the terminus of the draw lumen is at the end of the curved tip, and thus is shielded from direct contact with a side wall of the blood vessel into which the catheter is inserted. This configuration lessens risks associated with prior art vascular access catheters, including occlusion of the catheter and damage to the vein wall.

6 Claims, 2 Drawing Sheets

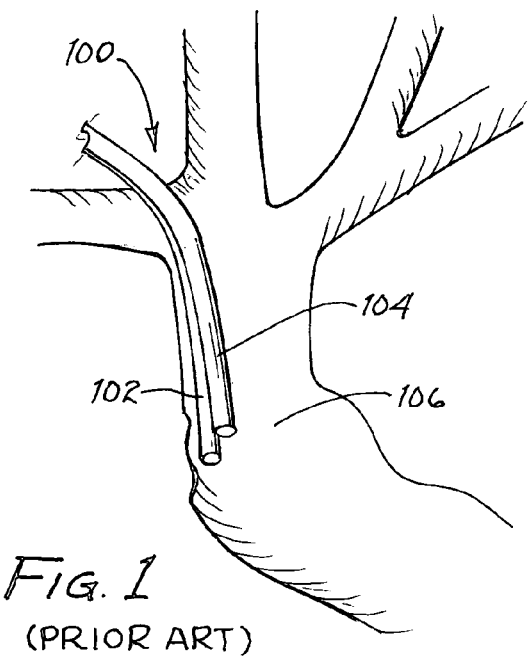
Fig. 1
(PRIOR ART)
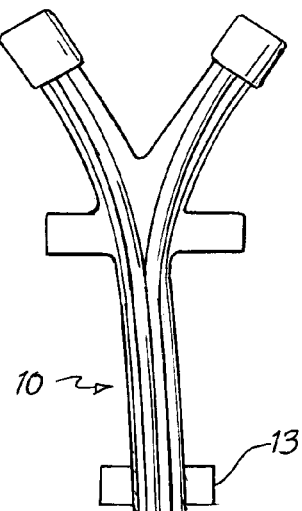
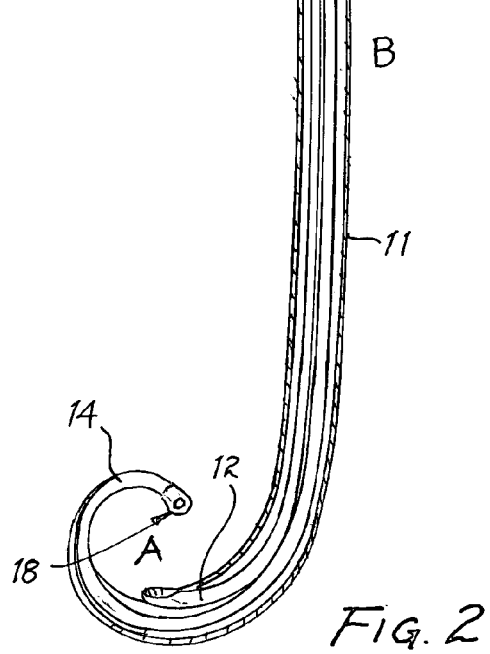
Fig. 3
Fig. 2

VASCULAR ACCESS CATHETER HAVING A CURVED TIP AND METHOD

BACKGROUND OF THE INVENTION

1. Field of the Invention

This invention relates to vascular access catheters for use in kidney dialysis generally and, more particularly, to a vascular access catheter having a curved tip and method therefor.

2. Description of the Prior Art

For persons whose kidney function is sufficiently impaired that they are unable to excrete nitrogenous wastes, regulate pH, or adjust ion concentrations in blood plasma, it is necessary to clean the blood artificially by dialysis. In general terms, dialysis involves the withdrawal of blood from the patient, its passage through a selectively permeable membrane, and its return to the patient.

There are several different methods for obtaining access to the patient's bloodstream so that dialysis may be performed. One common method involves the use of a catheter, typically one having a double lumen, which is inserted into a vein. Commonly, the vascular access catheter is inserted into the subclavian, jugular or femoral veins.

However, because prior art catheters have a substantially axial bore, they permit the tip thereof to be positioned near the wall of the vein. As a result, there are a number of possible complications associated with the use of a vascular access catheter. For example, the catheter can contact the wall of the vein and become occluded. In addition, the suction of blood from the vein can cause endothelial injury, denude the lining of the vein wall, and trigger clot formation (possibly leading to occlusion of the vein and catheter). The return of blood to the vein, under pressure, can also harm the vein wall.

A need therefore existed for a vascular access catheter, to be used for dialysis, that reduces the risks of occlusion of the catheter, as well as the risk of harm to the vein. In particular, a need existed for a vascular access catheter having a curved tip so as to direct the catheter terminus away from the vein wall. The present invention satisfies these needs and provides other related advantages.

SUMMARY OF THE INVENTION

It is an object of this invention to provide a vascular access catheter, to be used for dialysis, that reduces the risks of occlusion of the catheter.

It is a further object of this invention to provide a vascular access catheter, to be used for dialysis, that reduces the risk of harm to the vein—including endothelial injury, denuding of the vein wall lining, and clot formation.

It is yet a further object of this invention to provide a vascular access catheter that has a curved tip to direct the catheter terminus away from the vein wall.

BRIEF DESCRIPTION OF THE PREFERRED EMBODIMENTS

In accordance with one embodiment of the present invention, a vascular access catheter is disclosed. The vascular access catheter comprises, in combination: a first catheter end coupled to a filtration apparatus; a second catheter end adapted to be inserted into a blood vessel; and a main body portion interposed between the first catheter end and the second catheter end; wherein the main body portion has an axial bore; and wherein the second catheter end is curved to define a curved tip area extending interiorly from an axis established by the axial bore of the main body portion.

In accordance with another embodiment of the present invention, a method for reducing risks associated with vascular access catheters is disclosed. The method comprising the steps of: providing a vascular access catheter comprising, in combination: a first catheter end coupled to a filtration apparatus; a second catheter end adapted to be inserted into a blood vessel; and a main body portion interposed between the first catheter end and the second catheter end; wherein the main body portion has an axial bore; wherein the second catheter end is curved to define a curved tip area extending interiorly from an axis established by the axial bore of the main body portion; and inserting the second catheter end into the blood vessel.

BRIEF DESCRIPTION OF THE DRAWINGS

FIG. 1 illustrates a prior art vascular catheter, inserted within a vein.

FIG. 2 is a front, cut-away view of a vascular catheter consistent with the present invention.

FIG. 3 is a front, cut-away view of an embodiment of the tip portion of a vascular catheter consistent with the present invention.

DETAILED DESCRIPTION OF THE PREFERRED EMBODIMENTS

Figure 4:
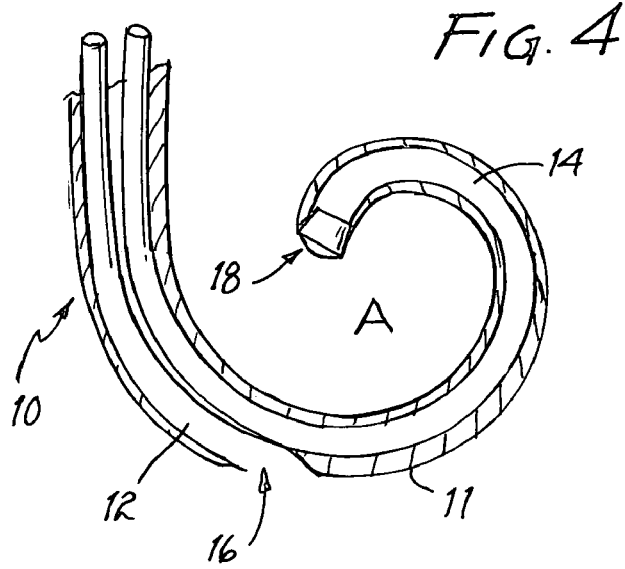
FIG. 4 is a front, cut-away view of another embodiment of the tip portion of a vascular catheter consistent with the present invention.
Figure 5:
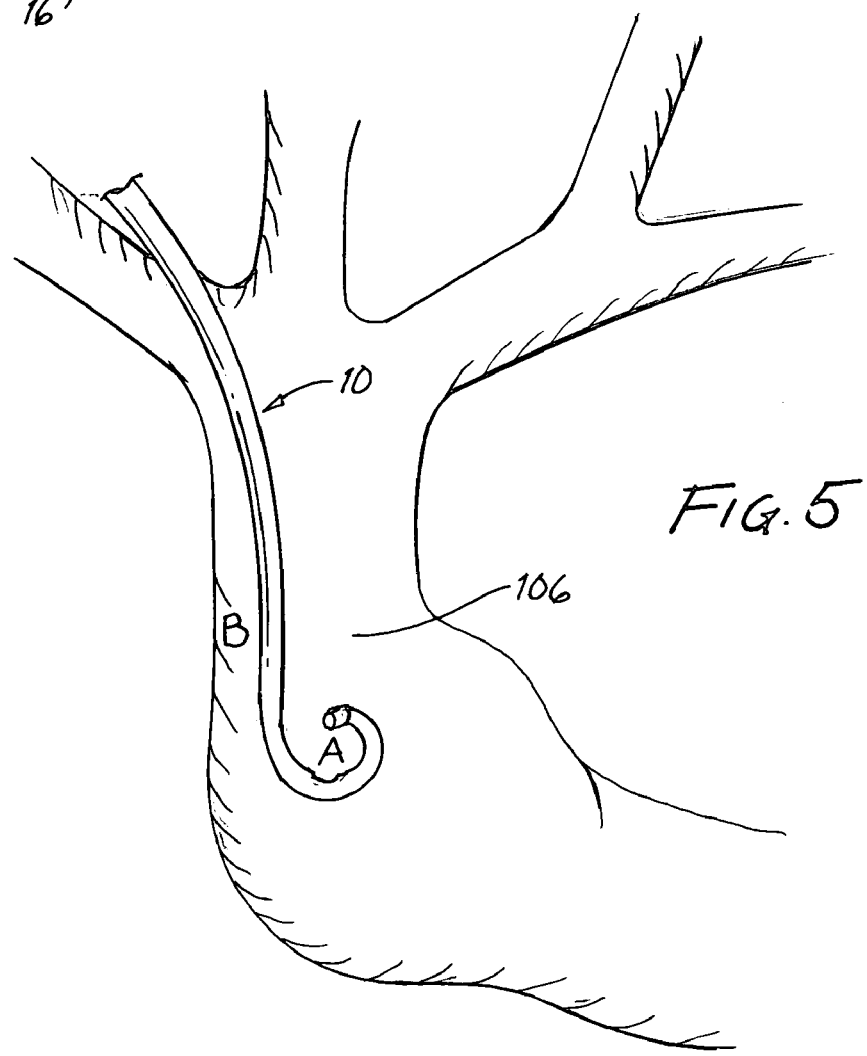
FIG. 5 illustrates a vascular catheter consistent with the present invention, inserted within a vein.

Referring first to FIG. 1, a prior art vascular catheter 100 is illustrated. The prior art catheter 100 is of the double lumen type, having a draw or arterial lumen 102 (usually located on the outside) and a return or venous lumen 104. The prior art catheter 100 operates as part of a dialysis system, with blood requiring filtration being removed through the draw lumen 102, undergoing filtration, and then being returned through the return lumen 104. FIG. 1 illustrates the insertion of the prior art catheter 100 into a vein 106. Vein 106 may be any desired vein, including for example the subclavian jugular or femoral veins, with the jugular vein currently being preferred.

As shown in FIG. 1, the prior art catheter 100 has a substantially axial bore. It therefore tends to be positioned within the vein 106 in such manner as to place one or both lumens 102 and 110 proximate the vein wall. This placement can clog the prior art catheter 100 or harm the vein 106, for example in one or more of the manners discussed above.

Referring now to FIGS. 2–5, embodiments of a vascular access catheter 10 consistent with the present invention are shown. As shown in these figures, the catheter 10 is of the double lumen type, wherein the two lumens are encased within sheath 11. However, it should be noted that the catheter 10 could also be single lumen.

As with the prior art catheter 100, the catheter 10 draws unfiltered blood from a patient, transports it to a filtration apparatus (not shown) for filtration, and returns it to the patient. The catheter 10 is inserted into the patient's body, and preferably has an anti-microbial cuff 13 that allows the person's tissue to grown into the catheter 10 and provide an improved seal. (The anti-microbial cuff 13 has been utilized with prior art catheters 100.)

Attention is particularly directed to the tip area A of the catheter 10. As shown herein, the tip area A has a generally pig-tail configuration with an opening at a distal end thereof and adapted to be inserted into a blood vessel. Preferably, a return lumen 12 terminates prior to the end of the pig-tail. It is further preferred that the draw lumen 14 terminate proximate the end of the pig-tail. (It is preferred to position the termination points of the lumens 12 and 14 sufficiently remote from one another so as to reduce recirculation of filtered blood.) Thus, while a main body portion B of the catheter 10 has an axial bore, the tip area A is curved to extend interiorly from an axis established by the axial bore of the main body portion B.

Further describing the tip area A shown in FIGS. 2–5, that area is looped so that a portion of a main body portion of the catheter 10 is lateral to the terminus 18 on two sides. (The terminus 18 may also be referred to herein as the distal end of the second catheter end.)

However, as shown in FIG. 4, it would be possible to position the terminus 16 of the return lumen 12 on the exterior of the tip area A. The advantage of this configuration would be the reduction of recirculation of filtered blood. Because the vacuum action of the draw lumen 14 is considered more potentially risk-creating for the catheter 10 and for the vein 106, it is more critical that the draw lumen 14 be positioned remote from the wall of the vein 106 than the return lumen 12.

As shown in each of FIGS. 2–4, the draw lumen 14 has its terminus 18 proximate the end of the pig-tail. This has the effect of preventing the terminus 18 of drawing in a direct manner proximate a wall of the vein 106, and alleviates the risks discussed herein.

While the invention has been particularly shown and described with reference to preferred embodiments thereof, it will be understood by those skilled in the art that the foregoing and other changes in form and details may be made therein without departing from the spirit and scope of the invention.

For example, while a pig-tail shaped is discussed herein for the tip area A, other shapes could also be practiced, so long as they had the effect of positioning the terminus of at least one lumen farther away from the vein wall than a prior art catheter 100. Other possible configurations would be a substantially J-shape, a substantially L-shape, or some modification thereof.

What is claimed is:

1. A vascular access catheter comprising, in combination:
   a first catheter end adapted to be coupled to a filtration apparatus;
   a second catheter end thereof having an opening at a distal end thereof and adapted to be inserted into a blood vessel;
   wherein said vascular access catheter has a draw lumen for transporting blood to said filtration apparatus and a return lumen for returning blood to said blood vessel;
   a main body portion interposed between said first catheter end and said second catheter end;
   wherein said main body portion has an axial bore; and
   wherein said second catheter end is looped so that a portion of said main catheter body is lateral to said second catheter end on two sides;
   wherein said draw lumen terminates at said second catheter end; and
   wherein said return lumen terminates prior to said second catheter end.

2. The vascular access catheter of claim 1 wherein a terminus of said return lumen is located on the interior of said looped second catheter end.

3. The vascular access catheter of claim 1 wherein a terminus of said return lumen is located on the exterior of said looped second catheter end.

4. A method for reducing risks associated with vascular access catheters comprising the steps of:
   providing a vascular access catheter comprising, in combination:
      a first catheter end adapted to be coupled to a filtration apparatus;
      a second catheter end having an opening at a distal end thereof and adapted to be inserted into a blood vessel;
      wherein said vascular access catheter has a draw lumen for transporting blood to said filtration apparatus and a return lumen for returning blood to said blood vessel; and
      a main body portion interposed between said first catheter end and said second catheter end;
      wherein said main body portion has an axial bore;
      wherein said second catheter end is looped so that a portion of said main catheter body is lateral to said second catheter end on two sides;
      wherein said draw lumen terminates at said second catheter end; and
      wherein said return lumen terminates prior to said second catheter end; and
   inserting said catheter second end into said blood vessel.

5. The method of claim 4 wherein a terminus of said return lumen is located on the interior of said looped second catheter end.

6. The method of claim 4 wherein a terminus of said return lumen is located on the exterior of said looped second catheter end.

* * * * *